United States Patent [19]

Meade

[11] Patent Number: 5,467,783
[45] Date of Patent: Nov. 21, 1995

[54] APPARATUS AND METHOD FOR THE REDUCTION OF SNORING

[76] Inventor: Thomas E. Meade, 215 16th St., SW., Albuquerque, N.M. 87104

[21] Appl. No.: 354,139

[22] Filed: Dec. 6, 1994

Related U.S. Application Data

[63] Continuation of Ser. No. 977,266, Nov. 16, 1992, abandoned.

[51] Int. Cl.$^6$ .................................................. A61F 5/56
[52] U.S. Cl. ........................... 128/848; 128/859; 128/861
[58] Field of Search ........................... 128/848, 857–863, 128/776, 777; 433/6, 7, 140

[56] References Cited

U.S. PATENT DOCUMENTS

| | | |
|---|---|---|
| D. 302,036 | 7/1989 | George . |
| 587,358 | 8/1897 | Anderson . |
| 746,869 | 12/1903 | Moulton . |
| 1,674,336 | 6/1928 | King . |
| 2,424,533 | 7/1947 | Faires . |
| 2,483,157 | 9/1949 | Singer . |
| 2,521,039 | 9/1950 | Carpenter . |
| 2,574,623 | 11/1951 | Clyde . |
| 2,590,118 | 3/1952 | Oddo, Jr. . |
| 2,627,268 | 2/1953 | Leppich . |
| 2,669,988 | 2/1954 | Carpenter . |
| 2,705,006 | 3/1955 | Cettel et al. . |
| 2,857,909 | 10/1958 | Johnson . |
| 2,882,893 | 4/1959 | Godfroy . |
| 3,126,002 | 3/1964 | Owens . |
| 3,132,647 | 5/1964 | Corniello . |
| 3,434,470 | 3/1969 | Strickland . |
| 3,457,916 | 7/1969 | Wolicki . |
| 3,478,742 | 11/1969 | Bohlmann . |
| 3,871,370 | 3/1975 | McDonald . |
| 4,144,614 | 3/1979 | Kesling . |
| 4,169,473 | 10/1979 | Samelson . |
| 4,185,817 | 1/1980 | Peterson . |
| 4,196,724 | 4/1980 | Wirt et al. . |
| 4,304,227 | 12/1981 | Samelson ............................. 128/860 |
| 4,431,411 | 2/1984 | Witzig et al. . |
| 4,495,945 | 1/1985 | Liegner . |
| 4,551,473 | 11/1985 | Schossow . |
| 4,553,549 | 11/1985 | Pope et al. . |

(List continued on next page.)

FOREIGN PATENT DOCUMENTS

| | | |
|---|---|---|
| 298649 | 11/1989 | European Pat. Off. . |
| 2320501 | 11/1974 | Germany . |
| 1569129 | 6/1980 | United Kingdom . |

OTHER PUBLICATIONS

"Dental Colleague" advertising material for 1988 seminars by Thomas E. Meade.
"Silent Night" advertising copy.
"Obstructive Sleep Apnea Synchrome: An Update for Dentists", Wayne W. Triplett, D.D.S. and Bruce A. Lund, D.D.S., Jan.–Feb. 1988.
"Treatment of Snoring with a Dental Orthosis", W. W. Schmidt–Nowara, T. E. Mease, R. V. Wiggins, Departments of Medicine and Surgery, University of New Mexico, Albuquerque, N.M., May 8–11, 1988.
"The NAPA Appliance", Great Lakes Orthodontics, Ltd., Handouts from May–Jun., 1992, meeting of Association of the Professional Sleep Society, pp. 25–27, 30–31.
Brochure: "The NAPA Appliance" (Nocturnal Airway Patency Appliance), Dr. Peter T. George.

Primary Examiner—Robert A. Hafer
Assistant Examiner—David J. Kenealy
Attorney, Agent, or Firm—Burns, Doane, Swecker & Mathis

[57] ABSTRACT

An apparatus for intra-oral use including a framework having an upper curved platform and a lower curved platform, each of the platforms being defined by two walls extending from and separated by a floor, a material bonded to the upper and lower curved platform adapted to be molded in a shape suitable for relatively snugly receiving maxillary teeth of a user and for relatively loosely receiving mandibular teeth of the user when the user's mouth is closed in a normal, closing arch, and a cavity formed between the upper and lower platforms adapted to receive the tongue of the user.

10 Claims, 3 Drawing Sheets

U.S. PATENT DOCUMENTS

| | | |
|---|---|---|
| 4,568,280 | 2/1986 | Ahlin . |
| 4,593,686 | 6/1986 | Lloyd . |
| 4,669,459 | 6/1987 | Spiewak . |
| 4,715,368 | 12/1987 | George . |
| 4,901,737 | 2/1990 | Toone . |
| 4,955,393 | 9/1990 | Adell . |
| 5,003,994 | 4/1991 | Cook ........................................ 128/848 |
| 5,092,346 | 3/1992 | Hays et al. ............................... 128/848 |
| 5,117,816 | 6/1992 | Shapiro et al. . |
| 5,154,184 | 10/1992 | Alvarez ................................... 128/848 |
| 5,174,284 | 12/1992 | Jackson . |
| 5,277,202 | 1/1994 | Hays . |
| 5,277,203 | 1/1994 | Hays . |

APPARATUS AND METHOD FOR THE REDUCTION OF SNORING

This application is a continuation of application Ser. No. 07/977,266, filed Nov. 16, 1992, now abandoned.

BACKGROUND OF THE INVENTION

The present invention relates to an oral apparatus for use in the treatment of snoring, and particularly to a dental orthosis for use during sleep to treat snoring.

Laypeople are commonly familiar with the symptoms of snoring, so little need be said in this regard. In mild cases, it may be a cause of amusement and only minor inconvenience. In more severe cases, however, it can disrupt sleep and even be a manifestation of a serious condition such as obstructive sleep apnea (OSA) syndrome, in which the sufferer must be awakened.

The major methods of treatment and aids to patients with obstructive problems of breathing were developed by Friedrick von Esmarch. As a military surgeon during the many wars in central Europe in the 19th century, he observed that many battlefield deaths occurred due to blood loss and/or strangulation. The principles that he developed to maintain an airway are still the primary principles in use today.

The simple, if somewhat crude, method that he used was to pull the tongue forward and to maintain this position by placing a skewer through the exposed part. This accomplished three major changes that form the principles which he recorded. The tongue was forward and largely clear of the throat, the jaws were open, and the lower jaw was moved forward. These three actions provided a considerable increase in the available airway of the oral pharynx.

Von Esmarch made another oral device which fitted to the teeth of the upper and lower jaw and by using his previously developed principles, this device produced a more open airway without pain or injury to the tongue.

Almost all devices developed and used for this purpose during the twentieth century employ the same basic form and functions of the von Esmarch device. The advent of modern dentistry has permitted refinement and improvements which enhance the aid to the patient with increased tolerance and comfort. There have been many patents issued for devices to help control snoring and obstructive sleep apnea. Most of them follow the von Esmarch principles.

For example, U.S. Pat. No. 1,674,336 to King discloses a respirator which includes upper and lower channels to support the upper and lower teeth respectively. The device is provided with a central air passage which opens into the channels through which air is exhaled. Projections are provided integral with an upper portion of the body of the device, defining between them an air channel. In theory, these projections support the tongue so that it does not block the air passages. In practice, however, this device is ineffective since the position of the tongue is such that the air passages are blocked.

At least one device provides a tongue chamber in front of the mouth. By creating a vacuum in this chamber, the tongue is held forward into the chamber. The device is held in place by fixation to the teeth of the upper jaw. A similar type of device, disclosed in U.S. Pat. No. 4,304,227 to Samelson, includes channels for insertion of the upper and lower teeth and a socket into which the tongue is inserted. The tongue is held in place in the socket. The Samelson device prevents air from escaping from the patient's mouth by a front plate which, when inserted, fits over the exterior portion of the patient's lips. The jaws are locked together during use and the tongue is prevented from resting in its normal position. This type of device may cause problems if the patient's nasal passages are clogged or if the patient coughs or vomits during sleep.

U.S. Pat. No. 4,715,368 to George discloses a device which includes upper and lower channels, including depressions into which the teeth fit. A beak with an orifice at the front end is provided in the center of the mouthpiece which parts the lips to allow air to pass through. The tongue is held in place by flanges extending inwardly from the lower channel. This device has attendant disadvantages in that it locks the jaws together and advances the lower jaw forward causing mandibular repositioning. This can cause aggravation of temporomandibular joint problems and wearer discomfort.

Another type of device is disclosed in U.S. Pat. No. 4,901,737 to Toone. This device is a form of the von Esmarch device but with a marked exaggeration of opening of the jaw wedge. This type of device, which is completely open in the front and preferably open at the top, across the palatal arch, requires mouth breathing, and so causes many complications, such as excess salivation and/or dry mouth. Such a device would be contraindicated in moderately severe or severe OSA. This device locks the jaws together and also repositions the mandible in an open and protrusive position, as compared with the normal closed position of the jaw. This displacement can cause discomfort and aggravate problems with the tempomandibular joint.

U.S. Pat. No. 5,003,994, issued to Cook, discloses an oral apparatus for reducing snoring and preventing sleep apnea which has a rigid shell with an upper tray, a lower cam structure to advance the mandible structure (lower jaw) forward with respect to the maxilla structure (upper jaw), stops to hold the mouth partially open, and a soft resilient pliable socket inside of the tray. This device is fitted such that the mandible is advanced forward with respect to the maxilla. Thus, this device suffers from the same drawbacks as the Toone device regarding discomfort and potential tempomandibular joint problems.

U.S. Pat. No. 5,092,346 to Hays et at., provides a dental device which provides a channel for receiving the upper teeth and a ramp formed on the bottom portion to cam the lower jaw forward. The ramp surface engages the lower anterior teeth in a manner such that the lower jaw is moved into a more forward position than normal. This device, by displacing the lower jaw in a more forward position, also may cause problems with the tempomandibular joint and pain and discomfort during use.

Both the Cook and the Hays et al. patents include breathing apertures between the upper and lower channels. These apertures are closed by the natural movement of the tongue during use.

U.S. Pat. No. 5,117,816 to Shapiro et at. provides an anti-snoring device which includes an upper surface portion which substantially covers all the upper teeth and a lower surface portion which contacts substantially all the lower teeth. An airway passage is provided in the center of the mouthpiece to permit breathing. The device includes a downwardly extending flange intended to extend into the lingual (tongue side of the teeth) vestibule of the user to maintain a forward posture of the lower jaw. This device also may cause pain and discomfort during use due to the forward placement of the jaw.

Though not designed as anti-snoring devices, mouthguards, such as those sometimes used by athletes, provide upper and lower channels into which the teeth are inserted. The pliant material used to form the mouthguards are fitted to the individual by insertion into the person's mouth, after having been heated to soften the material. These devices are not suitable for use as anti-snoring devices since they provide no means by which the tongue is held in a forward position so as to prevent blockage of the esophageal airway. There is no space provided at all sufficient to receive the tongue between the upper and lower channels. Additionally, these devices serve to lock the jaws together and prevent natural movement.

SUMMARY OF THE INVENTION

It is an object of the present invention to provide a method and apparatus for reducing snoring that overcomes the above described disadvantages.

According to one embodiment of the present invention, an apparatus for intra-oral use is provided comprising upper means for snugly fitting over anterior maxillary teeth of a user, lower means, integral with the upper means, for loosely fitting over anterior mandibular teeth of the user so as to allow the mandibular teeth to approach the maxillary teeth and come to rest in a closing normal arch and to allow complete freedom of movement of the mandible in forward and side-to-side directions while preventing rear movement of the mandible, and means for receiving the tongue of the patient disposed between, and integral with, the upper and lower means.

According to one embodiment of the present invention, an apparatus for intra-oral use is provided comprising a framework having an upper platform and a lower platform, each of the platforms being defined by two walls separated by a floor, a material bonded to the upper and lower platforms adapted to be molded in a shape suitable for relatively snugly receiving maxillary teeth of a user and for relatively loosely receiving mandibular teeth of the user when the user's mouth is closed in a normal closing arch, and a cavity formed between the upper and lower platforms adapted to receive the tongue of the user.

According to one embodiment of the present invention, a method is provided for reducing snoring in a wearer comprising, providing a framework for insertion into the mouth of the wearer having upper and lower channels to accommodate upper and lower teeth in a normal closing arch of the wearer's mouth, preventing backward movement of the lower jaw by providing a flange on a lower portion of the framework, and providing a cavity to receive the tongue such that the base of the tongue is rotated downward and forward to open the esophageal airway.

Still other objects, features and attendant advantages of the present invention will become apparent to those skilled in the art from a reading of the following detailed description of the embodiments constructed in accordance therewith, taken in conjunction with the accompanying drawings.

BRIEF DESCRIPTION OF THE DRAWINGS

The invention of the present application will now be described in more detail with reference to the preferred embodiments of the device, given only by way of example, and with reference to the accompanying drawings, in which.

GENERAL DESCRIPTION OF THE PREFERRED EMBODIMENTS

The present invention relates to an oral apparatus for use in the treatment of snoring, and particularly to a dental orthosis for use during sleep to eliminate or substantially reduce loud snoring. The anti-snoring device according to the present invention consists of a substantially semi-circular hard shell or framework that holds a soft, moldable thermoplastic material. The molded material forms snugly over the anterior maxillary (upper) teeth, thus preventing the appliance from being dislodged. The mandibular (lower) anterior teeth will fit loosely into the moldable material in such a way that the lower jaw can open, close and move from side to side.

The hard framework with a thin layer of moldable material extends posteriorly over the bicuspids and molars in such a way as to prevent supra eruption of these teeth. The anti-snoring device according to the present invention is designed and fitted to allow the mouth to close in the normal arch of closure and not to forcefully thrust the mandible forward to prevent trauma to the tempomandibular joint and discomfort during use. This new device also allows complete freedom of movement of the mandible side to side, but does not allow the mandible to drop backwards. The device also allows voluntary, natural movement of the lower jaw forward while not forcing such forward movement.

The hard shell of the appliance has an area between the anterior maxillary and mandibular teeth into which the tongue protrudes during use. Thus, by opening the jaws slightly, enough for the tongue to move forward into the global cavity provided for it, the base of the tongue will be rotated downward and forward, opening the airway. This opening of the airway is further enhanced by the natural reflex of the tongue to slide forward into the cavern between the front teeth, with the resulting elimination or substantial reduction of snoring.

This appliance is safer than previous oral anti-snoring appliances, since the two jaws are not "locked" together, allowing the wearer to sneeze, cough, or even vomit, around the appliance and not aspirate. The channel which is provided along the outer side of the appliance in a preferred embodiment of the appliance facilitates oral breathing if the nasal passages are closed. However, with a normal patent opened nasal airway, the appliance discourages oral breathing and permits proper nasal breathing.

DETAILED DESCRIPTION OF THE PREFERRED EMBODIMENTS

Figure 1:
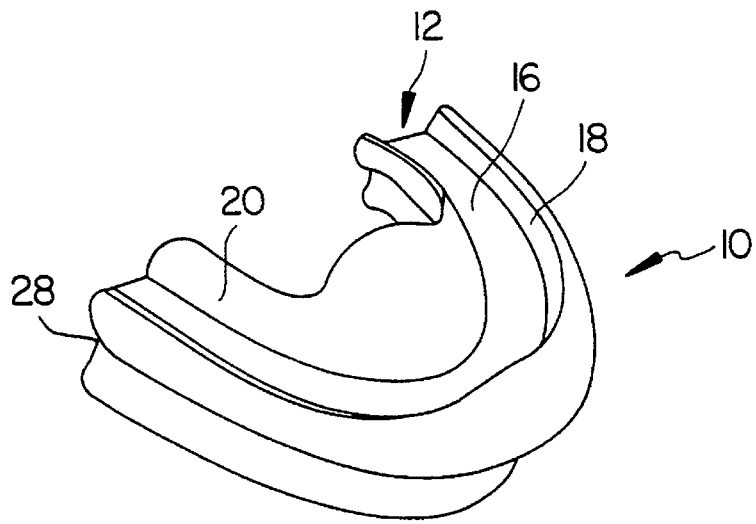
FIG. 1 is a perspective view of the shell of the apparatus according to the present invention.

FIG. 1 is a perspective view of the shell 10 of the apparatus according to a preferred embodiment of the present invention. The semi-circular shell 10 is made of a rigid or semi-rigid material which may be injection molded to create the desired shape. A single piece of plastic may be used to form the shell. One such material is methylmethacrylate, which is a plastic material used for dentures. After the device is fitted, it may be cured. The curing process prevents undesirable absorption of mouth fluids, or cleaning fluids, and presents a smooth non-irritating surface to the soft tissues of the mouth.

Alternatively, according to a preferred embodiment, this device may be made from a resilient semi-rigid polycarbonate resin thermoplastic. The resin preferably has a specific gravity of about 1.20, a tensile strength (yield) of about 9000 and a softening temperature of about 310° F. One such material is sold by General Electric Company under the trademark Lexan™, though other comparable materials may be used.

For purposes of ease of description, the terms upper, lower, front and rear have been used. It is understood that these relative terms describe the device in its normal in-use position. That is, upper and lower refers to the portions of the apparatus which receive the maxillary and mandibular teeth respectively, front refers to that portion of the device facing the outside of the mouth and rear refers to that portion facing the rear of the mouth toward the throat.

Figure 2:
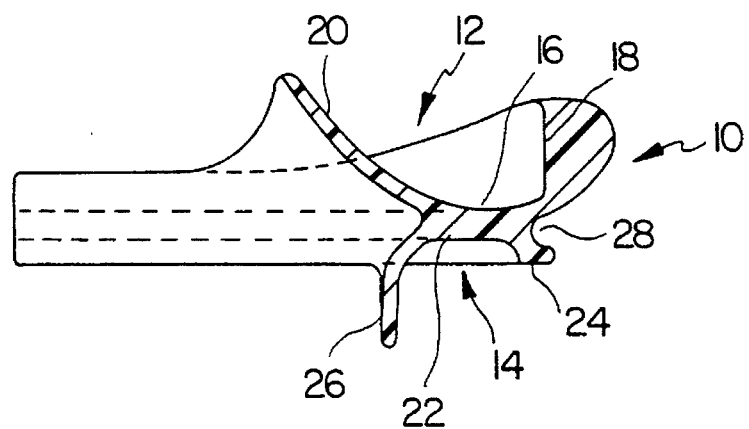
FIG. 2 is a cross-sectional view of the shell of the apparatus according to the present invention.

Referring to FIGS. 1 and 2, the shell 10 is provided with upper and lower platforms 12 and 14, respectively. The upper platform 12 is defined by front and rear walls or flanges 18 and 20, respectively, extending upwardly from the platform floor 16. The lower platform 14 is defined by front and rear walls or flanges 24 and 26, respectively, extending downwardly from the platform floor 22. The rear flange 26 extends substantially perpendicular with respect to the floor 22 of the lower platform 14. At the intersection of the front sides of the upper front wall 18 and the lower front wall 24, an outer channel 28 is formed around the outer circumference of the apparatus. The front side of the shell 10 is solid, and impervious to air. In particular, there is no aperture to permit breathing through the device when the device is positioned in the mouth. If the wearer wishes to breathe through the mouth at all, it is necessary to draw air around the periphery of the device as described below.

Figure 3:
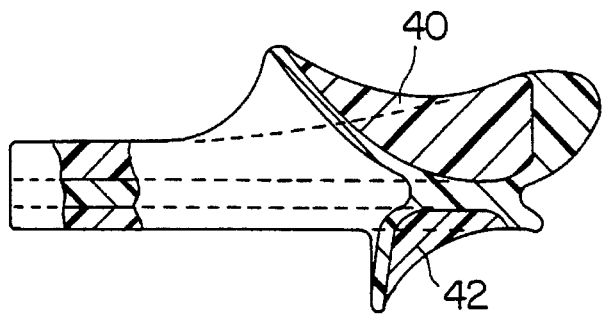
FIG. 3 is a cross-sectional view of the shell of the apparatus fitted with a moldable material according to the present invention.

Resin layers 40, 42, respectively, are bonded to the platforms 12 and 14 (FIG. 3). These layers may be formed from an ethylene-vinyl acetate copolymer resin, and preferably from a resin having a softening and molding temperature of about 150° F. One such material is sold by the Du Pont Company under the trademark Elvax™.

According to a preferred embodiment of the present invention, the resin layers are formed from material which can be easily molded in the user's mouth and thus conform to the configuration of the user's upper teeth and normal closing arch. This results in significant cost savings due to a reduction in the time required for fabrication, fitting, and adjustment of the device. Further, the fitting of the device to allow for retention of the normal closing arch of the user provides a significant advantage over other known devices. This advantage results from the elimination of the potential problems with the tempomandibular joint and the substantial increase in comfort for the user during use.

Individual fitting of the apparatus to fit the user's normal closing arch and teeth is simplified by the formation of the apparatus from a shell of a polycarbonate resin thermoplastic and having layers of acetate copolymer resin bonded thereto. According to a preferred embodiment, the acetate copolymer resin layer is about 3 to 4 millimeters in thickness in the platform. Preferably, the acetate copolymer resin has a substantially lower softening and molding temperature than that of the polycarbonate resin-thermoplastic forming the shell. This simplifies the individual fitting of the device to the user's mouth.

To fit the device to a particular user, the device is immersed in a hot fluid, preferably water, to impart a yielding nature to the acetate copolymer resin layer. In this manner, the resin layer accepts the user's distinctive tooth and dental closing arch configuration during the fitting process.

Once the acetate copolymer resin is sufficiently moldable, the device is forcibly inserted against the user's upper jaw and teeth. The user then closes his/her mouth in a normal manner. This causes the lower teeth to be pressed against the resin layer in the lower platform. Upon cooling to ambient temperature, the acetate copolymer resin retains the user's tooth configuration, for ease of repeat placement by the user. Excess resin can be cut from the device to make the device more comfortable in use.

It is important for the proper fitting of this device that the user is instructed to close his/her mouth normally, so that the fitted apparatus does not cause any unnatural forward movement of the lower jaw. In other words, when the apparatus according to the present invention is fitted in the user's mouth, the lower jaw is in substantially the same position as it is when the device is not inserted in the mouth, so that with respect to the upper jaw the normal closing arch of the user is maintained. When the fitted apparatus is inserted in the user's mouth, the device allows complete freedom of natural movement of the lower jaw side to side, but does not allow the lower jaw to drop backwards. However, as noted above, while forward movement of the lower jaw is permitted, the lower jaw is not forced into an unnatural forward placement during use.

When fitted properly, the anterior maxillary teeth are firmly engaged in the moldable material on the upper platform 12. The rest of the maxillary teeth back to approximately the first molars on each side have the occluding surfaces indented in the moldable material. The lower anterior teeth go into the area provided by the; lower platform 14. This area should only be a rest or a stop for these teeth, so that the jaw will not be allowed to close all the way to its normal point of closure. The fitted apparatus allows the jaw to move and barely has the teeth indented in it. The lower platform 14 extends back to about the first molars to prevent supra eruption of the teeth, to allow the jaws to be supported, and to prevent pain.

Figure 4:
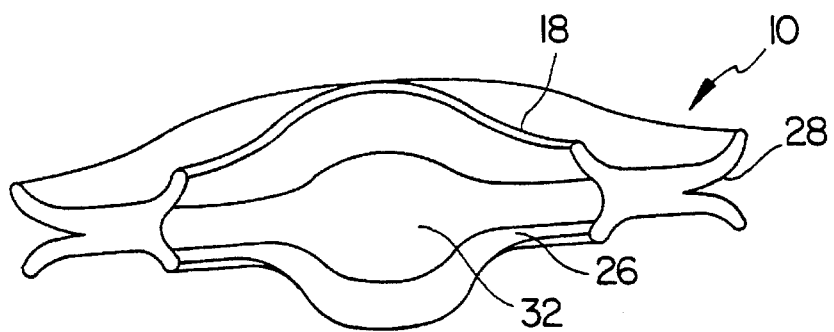
FIG. 4 is a rear view of the shell of the apparatus according to the present invention.

FIG. 4 illustrates a rear view of the shell 10 apparatus. As described above, a channel 28 is formed on the front side of the apparatus at the intersection of the upper front wall 18 and the lower front wall 24. The channel 28 forms an air passage around the outside of the apparatus when it is inserted during use. In the inside surface of the apparatus, a cavity 32 is formed at the intersection of the rear side of the upper rear wall 20 and the lower rear wall 26. The tongue rests in the cavity 32 by natural reflexive movement when the apparatus is in use to open the esophagal airway.

Figure 5:
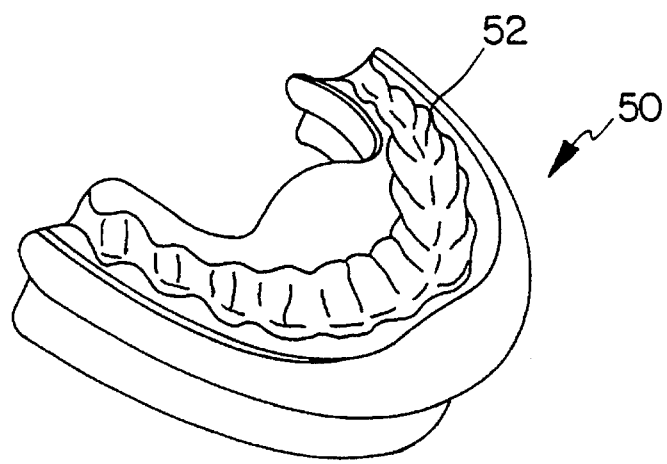
FIG. 5 is a perspective view of a fitted apparatus according to the present invention.

FIG. 5 illustrates an apparatus 50 which has been fitted to a user's mouth. Teeth impressions 52 are formed when the apparatus is inserted against the upper jaw and teeth as described above. The lower teeth also form impressions, which are not shown in the drawings.

Figure 6:
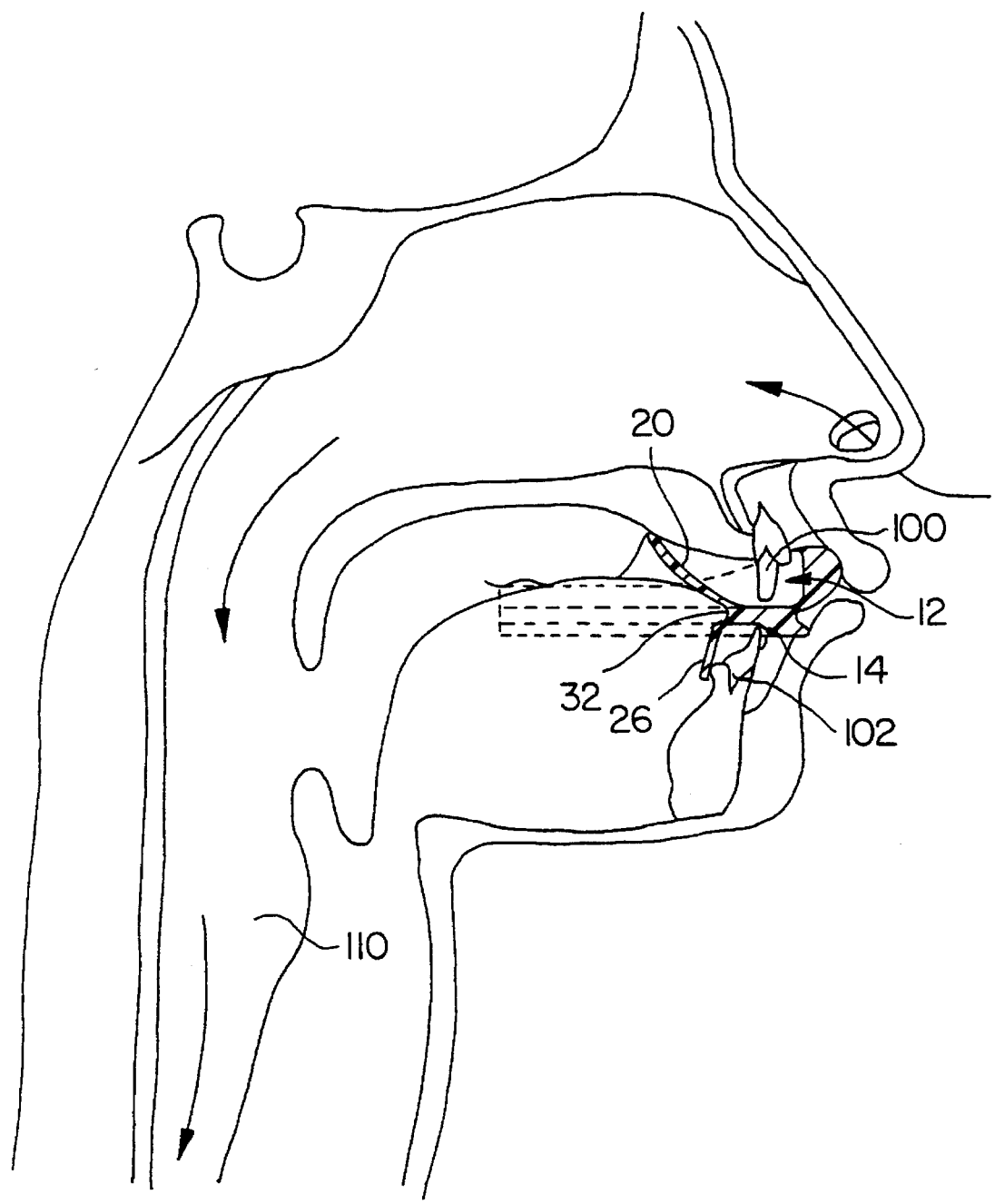
FIG. 6 is a cutaway view of the air passages of a person fitted with the apparatus according to the present invention.

FIG. 6 illustrates an apparatus in its in-use position in the mouth. For purposes of clarity, the resin layer has been omitted. The upper teeth 100 are snugly inserted in the impressions (not shown) in the upper platform 12. The lower teeth 102 rest in the impressions (not shown) in the lower platform 14 and are prohibited from backward movement by the wall or flange 26 of the lower platform 14. When the apparatus is inserted, the mandibular teeth approach the maxillary teeth and come to rest in a normal closing arch, with the jaws separated from each other by the apparatus. The user's tongue (not shown) slides into the cavity 32 formed by the rear portion of the wall 20 forming the upper platform 12 and the wall 26 forming the lower platform 14. Specifically, by opening the jaws slightly, an amount sufficient for the tongue to move forward into the cavity 32 provided for it, the base of the tongue is rotated downward and forward into the cavity 32 between the teeth, with the resulting opening of the esophageal air passageway 110.

The apparatus is constructed to fit loosely in the mouth so that the jaws are not locked together. In this manner the user can sneeze, cough or even vomit around the apparatus and not aspirate. The channel 28 formed around the outside of the apparatus by the upper and lower outer walls 18 and 24, respectively, facilitates oral breathing if the nasal passages are closed. However, with a normal patent nasal airway, as shown by the arrows on FIG. 6, the apparatus will discourage oral breathing and permit proper nasal breathing.

The foregoing description of the specific embodiments will so fully reveal the general nature of the invention that others can, by applying current knowledge, readily adapt for various applications such specific embodiments without departing from the generic concept, and, therefore, such adaptations and modifications should and are intended to be comprehended within the meaning and range of equivalents of the disclosed embodiments. It is to be understood that the phraseology of terminology employed herein is for the purpose of description and not of limitation.

What is claimed is:

1. An apparatus for intra-oral use comprising:
   a framework having an upper platform and a lower platform, each of the platforms being defined by two walls extending from and separated by a floor, a rear one of the two walls defining the lower platform extending substantially perpendicular to the floor defining the lower platform, said upper and lower platforms being curved in an arch to conform to a user's mouth, a rear wall of said lower platform being disposed at an inner portion of the arch and extending substantially perpendicular to a plane that contains the arch;
   a material bonded to the upper and lower platform adapted to be molded in a shape suitable for relatively snugly receiving maxillary teeth of a user and for relatively loosely receiving mandibular teeth of the user when the user's mouth is closed in a normal closing arch; and
   a cavity formed between the upper and lower platforms adapted to receive the tongue of the user.

2. The apparatus recited in claim 1, further comprising a channel disposed along an outer circumference of the framework formed at an intersection of an outer side of the front walls of each of the upper and lower platforms, the channel forming an air passage during use of the apparatus.

3. The apparatus recited in claim 1, wherein the framework is formed from a single piece of plastic.

4. The apparatus recited in claim 1, wherein the framework is formed from a resilient semi-rigid polycarbonate resin thermoplastic.

5. The apparatus recited in claim 4, wherein the thermoplastic is Lexan™.

6. The apparatus recited in claim 1, wherein the material bonded to the upper and lower platforms is an ethylene-vinyl acetate copolymer resin.

7. The apparatus recited in claim 6, wherein the material is Elvax™.

8. The apparatus recited in claim 1, wherein a front one of the two walls defining the lower platform is shorter than the rear one of the two walls defining the lower platform.

9. The apparatus recited in claim 1, wherein a rear one of the two walls defining the lower platform forms a stop such that the mandibular teeth are prevented from rearward movement during use.

10. The apparatus recited in claim 1, wherein a front side of the apparatus between the upper and lower means is a solid wall which is impervious to air and the cavity in which the tongue is received is formed on a rear side of the solid wall.

* * * * *